(12) United States Patent
Disch et al.

(10) Patent No.: US 6,316,521 B1
(45) Date of Patent: Nov. 13, 2001

(54) ABSORPTION OF FORMALDEHYDE IN CLOSED, GASTIGHT PACKS

(75) Inventors: Stefan Disch, Frankfurt; Tilo Vaahs, Idstein, both of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/722,969

(22) Filed: Nov. 27, 2000

(30) Foreign Application Priority Data

Nov. 29, 1999 (DE) .............................................. 199 57 439

(51) Int. Cl.⁷ .................................................. G01G 45/12
(52) U.S. Cl. .......................... 523/102; 423/599; 428/688
(58) Field of Search ........................... 423/599; 523/102; 428/688

(56) References Cited

U.S. PATENT DOCUMENTS

| | | | |
|---|---|---|---|
| 4,001,372 | * 1/1977 | Okabe et al. | 423/235 |
| 5,284,892 | * 2/1994 | Brode, III et al. | 524/251 |
| 5,413,827 | * 5/1995 | Brodie, III et al. | 428/35.7 |

\* cited by examiner

*Primary Examiner*—Kriellion A. Sanders
(74) *Attorney, Agent, or Firm*—Connolly Bove Lodge & Hutz LLP

(57) ABSTRACT

A small amount of an absorber mixture comprising activated aluminum oxide and potassium permanganate deodorizes the space within closed, gastight packs, in particular the space within packs of the type in which objects or materials which comprise polyacetal or otherwise release formaldehyde are present. Deodorization here is the removal (i.e. elimination or absorption) of volatile constituents emerging from plastic moldings or from plastic materials, in particular cleavage products, such as formaldehyde. The process is particularly suitable for the packaging of moldings or of assemblies which are to be used in the medical sector, in the food and drink sector or in any other sector affecting health.

9 Claims, No Drawings

ABSORPTION OF FORMALDEHYDE IN CLOSED, GASTIGHT PACKS

The invention relates to a process for absorbing formaldehyde in closed, gastight packs, and also to the use of a mixture comprising a specific metal oxide and comprising permanganate, for removing formaldehyde from the enclosed gas space of closed, gastight packs. The process of the invention can be applied to the packaging of formaldehyde-releasing plastics, such as polyacetals, phenol-formaldehyde resins (Bakelite) or melamine-formaldehyde resins, and in particular to acetal-containing plastics.

Residual constituents of volatile substances or of cleavage products, in particular formaldehyde, frequently remain within pellets or moldings made from polyacetal after these have been produced, and these constituents diffuse out from the pellets or molding in the course of time. As far as possible, therefore, pellets or moldings are stored in a free contact with the atmosphere so that they can be flushed by air. However, it is essential for many applications, in particular in the medical sector, for the molding produced, or an assembly with one or more moldings made from polyacetal, to be transferred immediately into closed packaging, frequently using gastight packaging materials.

Quite irrespective of whether this packaging is packaging filled with air, with a gas or with a gas mixture, or is vacuum packaging in which no gas is present, the abovementioned volatile substances and cleavage products diffuse out from the pellets or from the molding in the course of time, and accumulate in a space within the packaging. If the packaging is subsequently opened, the accumulated volatile substances and cleavage products suddenly escape, and in doing so generally propagate an odor which is to some degree unpleasant.

Similar problems arise in the packaging of other polyacetal-containing or formaldehyde-releasing objects or materials in closed, gastight packaging (i.e. packs).

The object was then to find a way of packing polyacetal-containing or formaldehyde-releasing objects or materials in closed, gastight packs without causing accumulation of volatile substances and cleavage products, in particular formaldehyde, within the gas space of the packaging during its period in storage.

U.S. Pat. No. 5,284,892 and U.S. Pat. No. 5,413,827 disclose the use of polyalkylimides, in particular polethyleneimides (PAI) as formaldehyde scavengers for packaging in the food and drink sector. The PAI here, if desired together with an oxygen scavenger, is preferably incorporated into the packaging material, composed of an olefinic polymer.

There is a commercially available gas-filtration material in bead form (PURATEX: ATEX Filter, Sprockhovel) made from activated aluminum oxide and potassium permanganate, used for eliminating hazardous gases at the low ppm level. To this end, the filter material is charged to filter modules through which the crude gas is passed and freed from hazardous substances by oxidation.

It is also known that gaseous silicone compounds can be removed by activated aluminum oxide ($Al_2O_3$) (JP6269631 A), and also that nitrogen oxides can be removed using solutions comprising alkali metal manganates or alkali metal permanganates (U.S. Pat. No. 4,001,372).

The object is achieved by placing small amounts of an absorber mixture comprising activated aluminum oxide and potassium permanganate into the space within the packaging.

The invention therefore provides a process for deodorizing the space within closed, gastight packs, which comprises placing a small amount of an absorber mixture comprising activated aluminum oxide and potassium permanganate into the pack.

The deodorization here is the removal (i.e. elimination or absorption) of volatile constituents emerging from plastic moldings or from plastic materials, in particular cleavage products, such as formaldehyde.

The invention provides in particular the deodorization of the space within packs in which polyacetal-containing or other formaldehyde-releasing materials or objects are present.

Surprisingly, it has been found that even a small amount of the commercially available gas-filtration material PURATEX is sufficient not only to prevent accumulation of volatile oxidizable constituents, in particular cleavage products, such as formaldehyde, in closed, gastight packs in which there is no through-flow, but also indeed to reduce markedly the concentration of the formaldehyde in the pack. PURATEX has hitherto been used as a filtration medium in filtration arrangements in which there is through-flow. This use of PURATEX is directed at the elimination of oxidizable gaseous compounds, e.g. the elimination of ethanol, formic acid, ammonia, formaldehyde, sulfur dioxide or nitrogen monoxide.

It is generally also possible to use other materials made from a mixture comprising activated aluminum oxide and potassium permanganate. Activated aluminum oxide is understood as meaning porous aluminum oxide particles whose water content is from 0 to 0.5% by weight. These mixtures may also comprise activated carbon, water absorbers and/or other formaldehyde scavengers, such as polyalkyleneimides, etc. The mixtures preferably comprise from 80 to 99.999% by weight of activated aluminum oxide, from 0.001 to 20% by weight of potassium permanganate and from 0 to 10% by weight of activated carbon, based on the mixture of aluminum oxide and potassium permanganate.

The mixtures, if desired mixed with binder, may be pressed or processed to give pellets. Pellets, for example those composed of activated aluminum oxide and activated carbon in a mixing ratio of the invention, can also be immersed into an aqueous solution of potassium permanganate. Removal of the water by drying then gives a usable absorber.

It is also possible to mix an alkaline aqueous solution of aluminum oxide with an aqueous potassium permanganate solution, to remove the water and to dry the remaining solid, followed by pelletization.

It has been found to be advantageous to use pellets with a very small grain size from 1 to 1000 $\mu$m, preferably from 10 to 800 $\mu$m, particularly preferably from 50 to 500 $\mu$m, whereas in the case of filter systems with through-flow it is preferable to use coarse-grain materials with a grain size of from 500 $\mu$m to 5 mm. It is particularly advantageous to use fine-particle or ground pellets. If desired, porous pellets may also be used. The coarse-grained material used in filter systems with through-flow is also effective in formaldehyde absorption in closed packs, but the time consumed in destroying a given amount of formaldehyde is many times greater with coarse-grained pellets than with a smaller grain size.

It is advantageous for the material comprising the absorber mixture to be packed into an envelope made from gas-permeable material, for example into a small bag made from nylon or from Perlon. However, it is also possible for the absorber mixture to be accommodated in another way in the interior of the sealed pack, it being merely necessary to ensure that there is sufficient opportunity for the substances to be absorbed to reach the absorber mixture by diffusion. It is possible to apply the absorber mixture to the inner side of the gastight pack, for example.

The process of the invention is particularly advantageous when applied to the immediate packing of moldings injection-molded from polyacetal or from polyacetal-containing material, or of assemblies comprising moldings of this type. This applies in particular to moldings or assemblies which are to be used in the medical sector (e.g. inhalers, medical devices and implements, etc.) or in the food and drink sector or in any other sector affecting health.

Polyacetals, i.e. polyoxymethylene homo- and copolymers or polyoxymethylene blends, are widely known. There are many descriptions of their preparation, processing and use. Polyolefins, i.e. polyolefin homo- and copolymers or polyolefin blends, which are examples of materials which may be used as gastight packaging material, are also well known and have been fully described. There are also other gastight packaging materials, in some cases of multilayer structure, widely known among skilled workers in the field of packaging, and the process of the invention can therefore be readily applied to appropriate closed packs.

EXAMPLE

In each experiment, 10 injection-molded plaques (80× 60×1 mm, weight about 7.1 g per plaque) made from polyoxymethylene copolymer (Hostaform C 9021, Ticona GmbH, Frankfurt) were suspended on a metal bar immediately following their production. To ensure that the surface of each plaque is in direct contact with the gas space, between each pair of plaques a Raschig ring was placed as a spacer. The entire arrangement was placed, with and, respectively, without, PURATEX absorber, into a polyethylene bag (PE bag), which had been provided with a zip closure and was sealed so as to be gastight.

The formaldehyde concentration (FA conc.) in the bag was determined using a Dräger Quantimeter 1000, using Dräger tubes with sensitivity for concentration ranges from 0.2 to 5 ppm and from 2 to 40 ppm.

Experiment 1: No PURATEX added.

Experiment 2: 1 g of PURATEX added (pellets packed in gas-permeable Perlon film and added in the form of a small bag; average grain size from 500 μm to 5 mm).

Experiment 3: 5 g of PURATEX added (pellets packed in gas-permeable Perlon film and added in the form of a small bag; coarse-grain, average grain size from 500 μm to 5 mm Experiment 4: 1 g of PURATEX added (pellets packed in gas-permeable Perlon film and added in the form of a small bag; average grain size from 10 μm to 1 mm)

TABLE 1

Results from Experiments 1–4

| Time [h] | Experiment 1 FA conc. [ppm] | Experiment 2 FA conc. [ppm] | Experiment 3 FA conc. [ppm] | Experiment 4 FA conc. [ppm] |
|---|---|---|---|---|
| 0 | Production of injection-molded plaques at time 0 | | | |
| 1 | 10 | 20 | 10 | 15 |
| 2 | 15 | 15 | 30 | 5 |
| 3 | 15 | 5 | 5 | 3 |
| 4 | 20 | 5 | 5 | 2 |
| 5 | 25 | 5 | 5 | 2 |
| 6 | 40 | 5 | 5 | 1 |
| 22 | — | 2 | 1 | 1 |
| 30 | 35 | 2 | 1 | 1 |

Without addition of PURATEX, the formaldehyde concentration in the PE bag rises to 40 ppm within 6 hours and then remains constant within the accuracy of measurement. Addition of 1 g of PURATEX of average grain size from 500 μm to 5 mm causes the formaldehyde concentration to fall after a moderate period to 5ppm, after an initial rise, and to achieve as little as 2 ppm after 22 h. Addition of 5 g of PURATEX of average grain size from 500 μm to 5 mm and, respectively, of 1 g of PURATEX of average grain size from 10 μm to 1 mm gives a formaldehyde concentration of as little as 1 ppm after 22 h, this being in the region of the odor threshold for formaldehyde.

What is claimed is:

1. A process for deodorizing the space within closed, gastight packs, where a small amount of an absorber mixture comprising activated aluminum oxide and potassium permanganate is placed into the pack.

2. The process as claimed in claim 1, wherein the absorber mixture may, if desired, also comprise activated carbon, water absorbers and/or other formaldehyde scavengers, such as polyalkyleneimides.

3. The process as claimed in claim 1, wherein the pack comprises formaldehyde-releasing, and in particular polyacetal-containing, materials or moldings, and the concentration of volatile substances, in particular of cleavage products, such as formaldehyde, in the space within the pack is not durably increased by adding the absorber mixture.

4. The process as claimed in claim 3, wherein the concentration of formaldehyde in the space within the pack is durably restricted to not more than 5 ppm, preferably not more than 2 ppm.

5. Method of Use of an absorber mixture comprising activated aluminum oxide and potassium permanganate, and also, if desired, activated carbon, water absorbers and/or other formaldehyde scavengers, such as polyalkyleneimides, for deodorizing the space within closed, gastight packs.

6. Method of Use as claimed in claim 5, where the closed pack comprises a formaldehyde-releasing, and in particular polyacetal-containing, material or molding.

7. Method of Use as claimed in claim 5, wherein the concentration of volatile substances, in particular of cleavage products, such as formaldehyde, in the space within the pack is not durably increased by adding the absorber mixture.

8. Method of Use as claimed in claim 7, wherein in particular the concentration of formaldehyde in the space within the pack is durably restricted to not more than 5 ppm, preferably not more than 2 ppm.

9. Method of Use as claimed in any of claim 5 for deodorizing packaging in which moldings or assemblies for applications in the medical sector, in the food and drink sector, or in another sector affecting health, are present.

* * * * *

UNITED STATES PATENT AND TRADEMARK OFFICE
CERTIFICATE OF CORRECTION

PATENT NO. : 6,316,521 B1　　　　　　　　　　　　　　　　　　　　　　Page 1 of 1
DATED : November 13, 2001
INVENTOR(S) : Stefan Disch and Tilo Vaahs It is certified that error appears in the above-identified patent and that said Letters Patent is hereby corrected as shown below:

<u>Column 4,</u>
Line 52, delete "any of".

Signed and Sealed this

Second Day of April, 2002

Attest:

Attesting Officer

JAMES E. ROGAN
Director of the United States Patent and Trademark Office